US00PP19035P2

(12) United States Plant Patent
Kolster

(10) Patent No.: US PP19,035 P2
(45) Date of Patent: Jul. 15, 2008

(54) ***COTINUS* PLANT NAMED 'OLD FASHIONED'**

(50) Latin Name: *Cotinus coggygria*
Varietal Denomination: Old Fashioned

(76) Inventor: Henny Kolster, Laag Boskoop 100, Boskoop 2771 GZ (NL)

( * ) Notice: Subject to any disclaimer, the term of this patent is extended or adjusted under 35 U.S.C. 154(b) by 135 days.

(21) Appl. No.: 11/501,193

(22) Filed: Aug. 9, 2006

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent L Bell

(57) ABSTRACT

A new and distinct cultivar of *Cotinus coggygria* named 'Old Fashioned' that is distinguishable from all other varieties of *Cotinus* by its medium green foliage topped by the contrasting greyed-purple of the younger emerging leaves.

2 Drawing Sheets

Genus: *Cotinus.*
Species: *coggygria.*
Denomination: 'Old Fashioned'.

BACKGROUND OF THE INVENTION

The present invention relates to a new and distinct cultivar of Smoke Bush known botanically as *Cotinus coggygria* and referred to hereinafter by the cultivar name 'Old Fashioned'.

'Old Fashioned' was discovered by the inventor in a cultivated area of Boskoop, The Netherlands in 1989. The inventor selected 'Old Fashioned' as a single-seedling which was growing in a bed of seedlings of *Cotinus coggygria* which the inventor had raised from seed collected by the inventor from plants grown at the inventor's nursery.

*Cotinus coggygria* is a deciduous shrub that is used in the landscape. 'Old Fashioned' is distinguished from all other existing varieties of *Cotinus coggygria* known to the inventor by its mature blue-green leaves contrasted with the young emerging leaves which are greyed-purple in color and which first attracted the inventor as a novel characteristic. This growth coloration continues through the summer before becoming deciduous as winter approaches. The inventor considered that 'Old Fashioned' was further distinguished by the large size and pronounced roundness of its foliage compared to other varieties of *Cotinus* known to the inventor. 'Old Fashioned' blooms in the early summer although the yellow green flowers are of limited interest and lasting only a few days.

The first asexual propagation was carried out by the inventor in the summer of 1990 at the inventor's nursery in Boskoop, The Netherlands, using softwood cuttings. Since that time under careful observation, 'Old Fashioned' has been determined stable, uniform, and reproduces true to type in successive generations of asexual propagation.

SUMMARY OF THE INVENTION

The following characteristics represent the distinguishing traits of the new variety of *Cotinus coggygria* named 'Old Fashioned'.

1. The mature foliage of 'Old Fashioned' in spring and summer is blue-green.

2. The young emerging foliage of 'Old Fashioned' is a contrasting greyed-purple.
3. The leaves of 'Old Fashioned' are large and rounded.
4. 'Old Fashioned' blooms in the summer for a brief period and the flowers are yellow-green.
5. 'Old Fashioned' is deciduous.

BRIEF DESCRIPTION OF THE DRAWINGS

The accompanying colored photographs illustrate the overall appearance of the new variety.

FIG. 2 also shows the inflorescence of 'Old Fashioned' which appears briefly in late spring.

Figure 1:
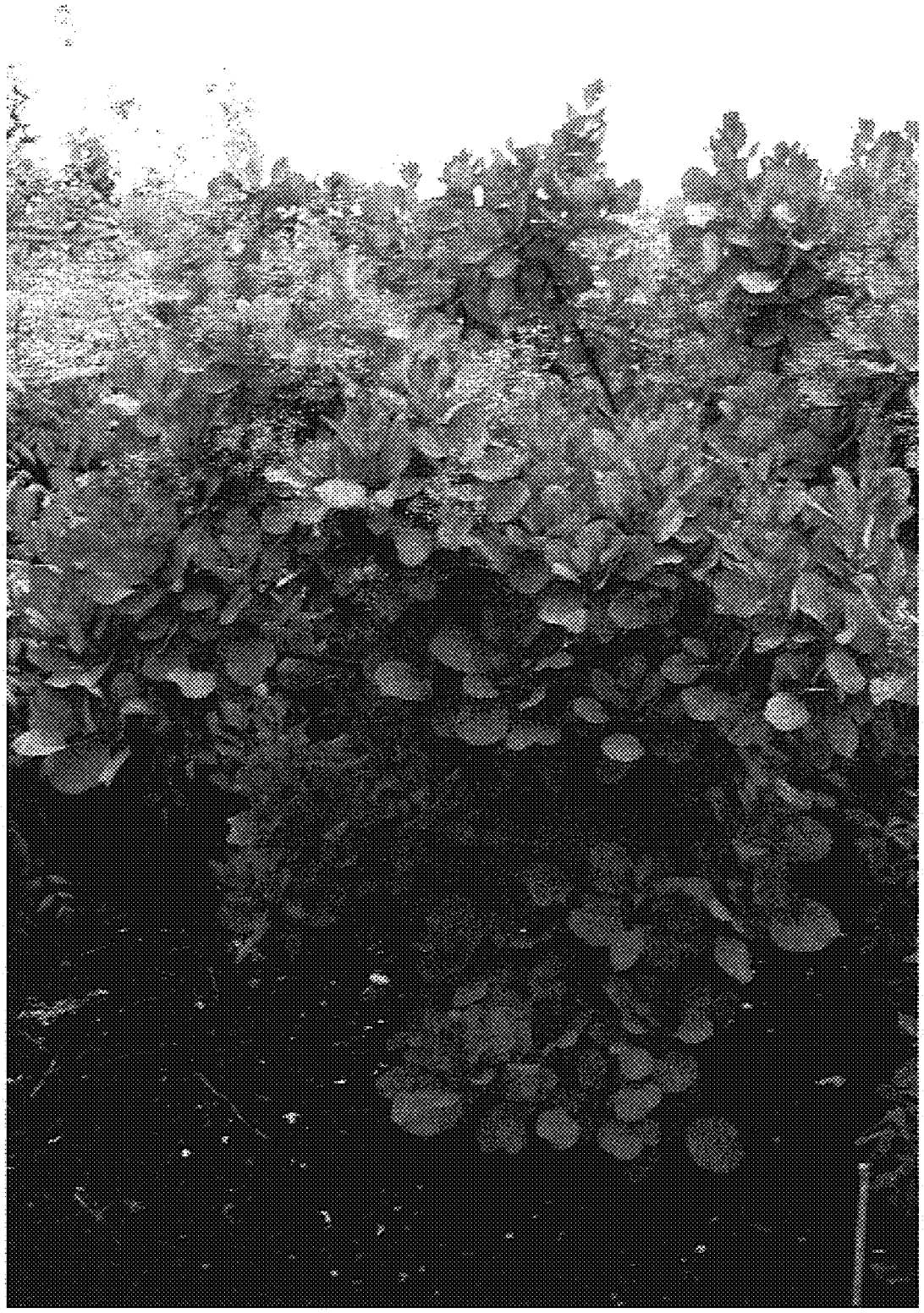
FIG. 1 shows a whole plant of 'Old Fashioned' growing in the ground at the inventor's nursery, Boskoop, Then Netherlands. The plants shown is six years old and was photographed in June 2006.
Figure 2:
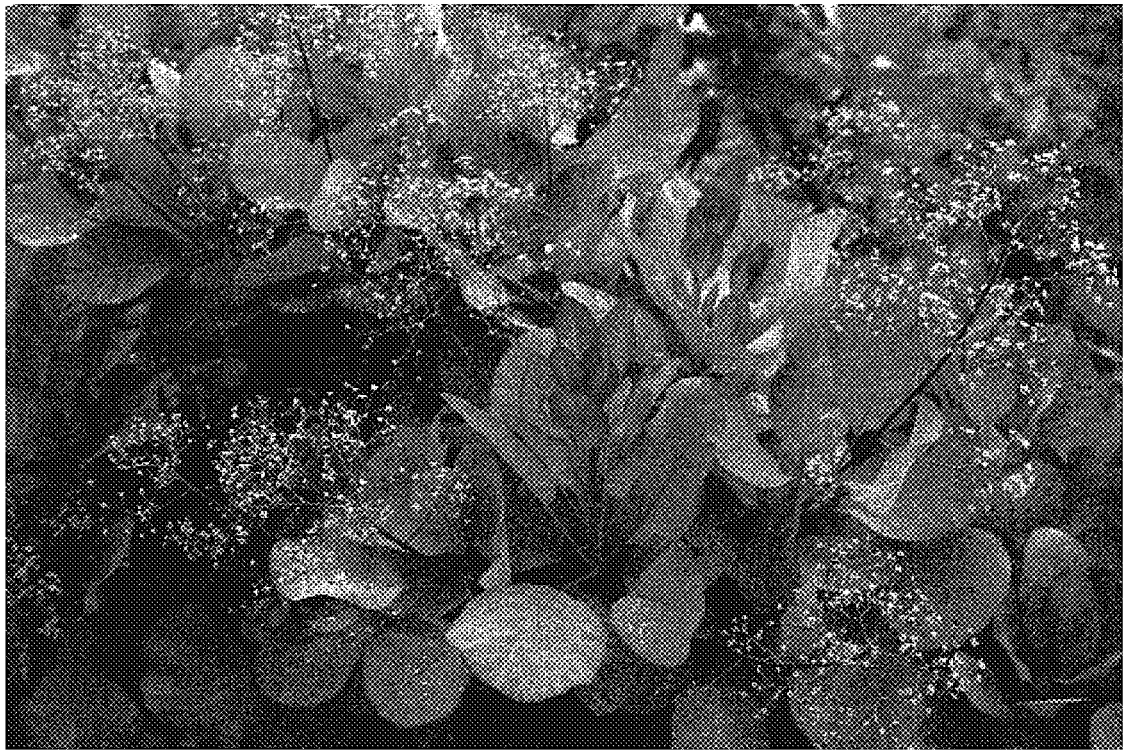
FIG. 2 shows a close-up view of the current year's new foliage growth on the plant depicted in FIG. 1.

The prints are made using conventional photographic techniques and although foliage colors in photographs may appear different from actual colors due to light reflectance, they are as accurate as possible by conventional photography.

BOTANICAL DESCRIPTION OF THE PLANT

The following is a detailed botanical description of the new cultivar of *Cotinus,* named 'Old Fashioned'. Observations, measurements, values, and comparisons were collected in Boskoop, The Netherlands in spring and summer 2006 from six year old plants grown in a field. The new *Cotinus coggygria* plant has not been observed under all possible environmental conditions. The phenotype may vary with variations in the environment such as temperature and light level, without, however, any variance in genotype. Color references are made to The Royal Horticultural Society Colour Chart except where general terms of ordinary dictionary significance are used. The growing requirements are similar to the species and no growing problems have been observed.

Botanical classification: *Cotinus coggygria* 'Old Fashioned'.
Common name: Smoke Bush.
Parentage: A seedling selection of *Cotinus coggygria* (not patented).
Propagation: Tissue culture and cuttings.
Type: Large deciduous shrub or small deciduous tree.
Use: Specimen plant.
Plant dimensions: 2 m in height and 1.5 m in width.
Shape: Irregular broad inverted triangle.
Growth habit: Broad upright.
Growth rate: Moderate.
Vigor: Moderate.
Seasonal interest: Spring, summer and fall foliage color.
Special needs: None observed.
High temperature tolerance: At least tolerant of temperatures of 35° C.
Low temperature tolerance: Hardy to USDA Zone 5.
Disease resistance and/or susceptibility: Not more resistant or susceptible to pests and diseases than other *Cotinus coggygria* varieties.
Soil types: Prefers dry or well-drained soils.
Light levels: Full sun.
Branching habit: Free branching.
Basal branching: Occasionally.
Number of lateral branches: Very many: in excess of 100.
Lateral branch dimensions: 30 cm in length and 6 mm in diameter.
Internode length: 0.9 cm.
Flowering season: Early summer.
Root system: Fine, spreading.
Cropping time: 12 weeks for a cutting to develop roots and 3 years to flower or finish in a 10 liter container or in the field.
Stem:
*Dimensions.*—1.5 m in length and 5 cm–8 cm in diameter.
*Appearance.*—Smooth, slightly glossy.
*Aspect.*—Rounded.
*Strength.*—Strong.
*Current year's growth.*—Ranges from 143C to 144A.
*Previous year's growth (bark present).*—N199A, N199C, both present.
*Pubescence.*—None.
Foliage:
*Leaf arrangement.*—Alternate.
*Compound or single.*—Single.
*Quantity of leaves per lateral branch.*—An average of 31.
*Leaves.*—Dimensions: An average of 8.9 cm in length and 7.0 cm in width. Shape: Orbicular. Margin: Entire, slightly undulate. Apex: Rounded. Base: Obtuse. Texture: Smooth, dull. Pubescence: Main and secondary veins sparsely covered with very short (an average of 0.5 mm) whitish green hairs too small to be color matched. Color of immature leaves (adaxial and abaxial surfaces): Ranges between 185C and 185D gradually replaced by 139C in veins, midrib and base as leaf ages. Color of mature leaves (adaxial): 119B. Color of mature leaves (abaxial): 139C. Venation pattern: Pinnate. Vein color of immature leaves (both surfaces): 139C. Vein color of mature leaves (both surfaces): 119C or slightly lighter than leaf color except midrib may sustain 185C until leaf fully mature. Durability to stress: High.
*Petioles.*—Dimension: An average of 4.1 mm in length and 1.5 mm in diameter. Color: Petiole color changes as leaf ages: Immature leaves (abaxial and adaxial surfaces): 139C. Recently matured leaves (abaxial and adaxial surfaces): 185C. Fully mature leaves (abaxial and adaxial surfaces): 119C.
*Foliage fragrance.*—Fresh and lemon-like.
Inflorescence:
*Flower arrangement.*—Terminal panicle.
*Inflorescence type.*—Panicle.
*Inflorescence dimensions.*—An average of 23.5 cm in height and 15.9 cm in width.
*Quantity of flowers per inflorescence/lateral stem.*—An average of 275.
*Quantity of flowers per plant.*—An average of 8000.
*Flower type or form.*—Single.
*Flower habit.*—Once a year in late spring.
*Natural flower season.*—Late spring, June.
*Rate of flower opening.*—Approximately 75% of the flowers open at the same time.
*Lastingness of flowers on plant.*—An average of 3 to 4 days.
*Lastingness of flowers off plant.*—Not applicable.
*Persistent or self-cleaning.*—Self-cleaning.
*Flower.*—Bud dimensions: An average of 1.5 mm in length and 1 mm in diameter. Bud shape: Oblong. Bud color: 150B. Rate of opening: Flower opens approximately 2 days after stage described. Dimensions: An average of 5 mm in diameter and 2 mm in depth. Aspect: Towards all directions. Shape: Rotate.
*Petal.*—Dimensions: An average of 2 mm in length and 1.5 mm in width. Appearance: Dull, smooth. Texture: Smooth. Arrangement: Rotate. Number: An average of 5. Fused or unfused: Unfused. Shape: Ovate. Margin: Entire. Tip: Acute. Base: Cuneate. Petal color (adaxial and abaxial surfaces): 150C fading to 150D. Petaloids: None.
*Sepal.*—Dimensions: An average of 1.8 mm in length and 1 mm in width. Appearance: Smooth, dull. Arrangement: Rotate. Number: An average of 5. Shape: Ovate, lower 40% fused. Margin: Entire. Tip: Acute. Base: Cuneate (fused). Color (immature, adaxial and abaxial sides): 144B and 144C. Color (mature, adaxial side): 144B. Color (mature, abaxial side): 144A.
*Calyx.*—Dimensions: An average of 1 mm in length and 3 mm in diameter. Shape: Campanulate.
*Peduncle.*—Dimensions: An average of 19.7 cm in length and 2.5 mm in diameter. Angle: Average of 0° (straight on top of lateral branch). Strength: Strong. Color: 138A.
*Pedicels.*—Types: Two types of pedicels are present. One type bears flowers; the other develops silky hairs. Dimensions (flowered pedicel): An average of 1.5 cm in length and 5 mm in diameter. Dimensions (flowerless pedicel): An average of 5 mm in length and 5 mm in diameter. Angle: Average of 45° away from the apical direction of the stem. Strength: Moderate. Color (flower pedicel): 144 A and 144B sparsely covered with short (average 0.8 mm) hairs colored N186C. Color (flowerless-pedicel): 144A to N186C densely covered with short (average 0.8 mm) hairs colored N186C.
*Reproductive organs.*—Stamen number: An average of 5. Anther shape and length: Kidney-shaped and an average of 0.3 mm in length. Filament length: An average of 1.2 mm. Anther color: 15A. Pollen amount: Low. Pollen color: 15A. Pistil number: An average of 1. Pistil length: An average of 0.2 mm. Stigma shape: Club-shaped. Stigma color: 144B. Style length: An average of 0.1 mm. Style color: 144B. Ovary color: 144B.

*Fruits and seeds.*—Quantity of fruit per lateral branch: An average of 275. Quantity of fruit per plant: An average of 8000. Fruit length: An average of 4 mm. Fruit diameter: An average of 4 mm. Fruit is flattened, average diameter at its flattest is 2 mm. Fruit color: Between 166A and 200B. Fruit texture: Smooth, glossy. Number of seeds per fruit: An average of 1. Seed dimensions: An average of 2 mm in length and 1 mm in diameter. Seed color: N200A.

It is claimed:

1. A new and distinct cultivar of *Cotinus coggygria* plant named 'Old Fashioned' as described and illustrated.

* * * * *